US012576433B2

(12) United States Patent
Shvetsov et al.

(10) Patent No.: US 12,576,433 B2
(45) Date of Patent: *Mar. 17, 2026

(54) METHOD AND APPARATUS FOR ATTACHMENT AND EVACUATION

(71) Applicant: Buffalo Filter LLC, Lancaster, NY (US)

(72) Inventors: Kyrylo Shvetsov, Depew, NY (US); Gregory Pepe, Lancaster, NY (US); Samantha Bonano, Williamsville, NY (US); Timothy Hersey, Tonawanda, NY (US); Joseph P. Callahan, Lancaster, NY (US)

(73) Assignee: Buffalo Filter LLC, Lancaster, NY (US)

( * ) Notice: Subject to any disclaimer, the term of this patent is extended or adjusted under 35 U.S.C. 154(b) by 634 days.

This patent is subject to a terminal disclaimer.

(21) Appl. No.: 16/929,915

(22) Filed: Jul. 15, 2020

(65) Prior Publication Data

US 2021/0060626 A1     Mar. 4, 2021

Related U.S. Application Data

(63) Continuation of application No. 15/379,175, filed on Dec. 14, 2016, now Pat. No. 10,751,768.

(Continued)

(51) Int. Cl.
*B08B 15/00*          (2006.01)
*A61B 18/00*          (2006.01)
(Continued)

(52) U.S. Cl.
CPC ............ *B08B 15/007* (2013.01); *A61B 18/00* (2013.01); *A61B 90/00* (2016.02);
(Continued)

(58) Field of Classification Search
CPC ......... A61M 1/00; A61M 27/00; A61F 13/00; A61F 13/02; A61F 15/00; A61B 90/00;
(Continued)

(56) References Cited

U.S. PATENT DOCUMENTS 2,064,344 A     12/1936  Good
3,321,970 A      5/1967  Walker, Sr. et al.
(Continued)

FOREIGN PATENT DOCUMENTS

DE          2806271 A1     8/1979

OTHER PUBLICATIONS

European Search Report of European Patent Application No. 16876602. 0, dated Jul. 12, 2019.

(Continued)

*Primary Examiner* — Rebecca E Eisenberg
*Assistant Examiner* — Timothy L Flynn
(74) *Attorney, Agent, or Firm* — Timothy W. Menasco, Esq.; Harter Secrest & Emery LLP

(57)          ABSTRACT

Presented are a method and apparatus for attachment and evacuation. The apparatus includes a housing having an opening, and a motor maintained within the housing, the motor operable to urge a fluid to pass through the opening. The apparatus further includes an adjustable element maintained within the opening, the adjustable element operable to change a size of the opening to a plurality of different diameters, and a knob moveably affixed to the housing, the knob operable to change the adjustable element to the plurality of different diameters.

11 Claims, 11 Drawing Sheets

Related U.S. Application Data

(60) Provisional application No. 62/267,123, filed on Dec. 14, 2015.

(51) Int. Cl.

| | |
|---|---|
| *A61B 18/14* | (2006.01) |
| *A61B 18/20* | (2006.01) |
| *A61B 90/00* | (2016.01) |
| *B01D 46/00* | (2022.01) |
| *B08B 15/04* | (2006.01) |
| *F24F 7/08* | (2006.01) |
| *H01R 24/68* | (2011.01) |
| *H01R 103/00* | (2006.01) |

(52) U.S. Cl.
CPC .......... *B01D 46/0041* (2013.01); *B08B 15/00* (2013.01); *F24F 7/08* (2013.01); *H01R 24/68* (2013.01); *A61B 18/14* (2013.01); *A61B 18/20* (2013.01); *A61B 2218/008* (2013.01); *B01D 2279/35* (2013.01); *B08B 15/04* (2013.01); *H01R 2103/00* (2013.01)

(58) Field of Classification Search
CPC .............. A61B 18/00; A61B 2218/008; B01D 46/0041; B08B 15/00; F24F 7/08; H01R 24/68

See application file for complete search history.

(56) References Cited

U.S. PATENT DOCUMENTS

| | | | | |
|---|---|---|---|---|
| 4,094,492 | A | 6/1978 | Beeman | |
| 4,986,839 | A | 1/1991 | Wertz | |
| 5,968,032 | A | 10/1999 | Sleister | |
| 5,971,977 | A | 10/1999 | Korenfeld | |
| 6,001,077 | A | 12/1999 | Ellman et al. | |
| 6,471,679 | B1 | 10/2002 | Suh | |
| 6,592,543 | B1 | 7/2003 | Wortwich | |
| 2005/0060974 | A1 | 3/2005 | Palmerton et al. | |
| 2005/0104024 | A1* | 5/2005 | Oliver | F16K 3/085 |
| | | | | 251/206 |
| 2005/0134037 | A1* | 6/2005 | Bruno | A47L 9/242 |
| | | | | 285/7 |
| 2009/0281482 | A1* | 11/2009 | Baker | A61M 1/77 |
| | | | | 604/35 |
| 2012/0109083 | A1* | 5/2012 | Coulthard | A61M 1/962 |
| | | | | 604/319 |
| 2013/0026753 | A1 | 1/2013 | Flanery | |
| 2014/0303576 | A1 | 10/2014 | Schultz | |
| 2014/0338529 | A1 | 11/2014 | Reasoner et al. | |

OTHER PUBLICATIONS

International Search Report of PCT Patent Application No. PCT/US2016/066678, completed Mar. 23, 2017.

* cited by examiner 53
50
56

54
57
55
56

METHOD AND APPARATUS FOR ATTACHMENT AND EVACUATION

BACKGROUND OF THE INVENTION

Field of the Invention

The present invention relates generally to the field of surgical smoke evacuation, and more particularly to a dual surgical smoke evacuation and universal hose attachment system and a method of using such a system for safe and efficient filtration of smoke plume generated by laser-surgical, electrosurgical, radiosurgical, cautery, hyfrecators and electrocautery devices.

Description of Related Art

Surgical smoke evacuation systems are designed to capture the smoke and plume generated during surgical procedures in which there is thermal destruction of tissue or bone. The plume from vaporized tissue contains small particles and gases that could be potentially hazardous. If not evacuated the materials can become airborne and deposit in the respiratory tracts of the surgical team. The type of surgical instruments, the characteristics of tissue, and the surgeon's technique affect the quantity and characteristics of the smoke plume.

BRIEF SUMMARY OF THE INVENTION

In view of the foregoing, it is an object of the present disclosure to provide a method and apparatus for attachment and evacuation.

A first exemplary embodiment of the present disclosure provides a method of evacuation. The method includes providing an evacuation system comprising housing having an opening, a motor maintained within the housing, the motor operable to urge a fluid to pass through the opening, an adjustable element maintained within the opening, the adjustable element operable to change a size of the opening to a plurality of different diameters, and a knob moveably affixed to the housing, the knob operable to change the adjustable element to the plurality of different diameters. The method further includes evacuating, by the motor, a fluid through the opening.

A second exemplary embodiment of the present disclosure provides an apparatus for evacuation. The apparatus includes a housing having an opening, and a motor maintained within the housing, the motor operable to urge a fluid to pass through the opening. The apparatus further includes an adjustable element maintained within the opening, the adjustable element operable to change a size of the opening to a plurality of different diameters, and a knob moveably affixed to the housing, the knob operable to change the adjustable element to the plurality of different diameters.

A third exemplary embodiment of the present disclosure provides an apparatus for evacuation. The apparatus includes a blower having a housing that maintains a motor, a user interface, an opening, a blower power supply, a filter, a blower connector, and an adjustable element, the motor operable to urge a fluid to pass through the opening and the adjustable element, the filter operable to filter extraneous materials from the fluid that passes through the opening and the adjustable element, the adjustable element operable to change a size of the opening to a plurality of different diameters, the user interface operable to control the motor. The apparatus further includes a pump having a housing that maintains a pump motor, a pump user interface, a pump port, a pump power supply, a pump connector, and a pump filter, the pump motor operable to urge a fluid to pass through the pump port, the pump filter operable to filter extraneous materials from the fluid that passes through the pump port, wherein the blower connector and the pump connector are operable to be coupled to each other thereby affixing the blower and the pump.

The following will describe embodiments of the present disclosure, but it should be appreciated that the present disclosure is not limited to the described embodiments and various modifications of the invention are possible without departing from the basic principles. The scope of the present disclosure is therefore to be determined solely by the appended claims.

BRIEF DESCRIPTION OF THE SEVERAL VIEWS OF THE DRAWING(S)

DETAILED DESCRIPTION OF THE INVENTION

Figure 1:
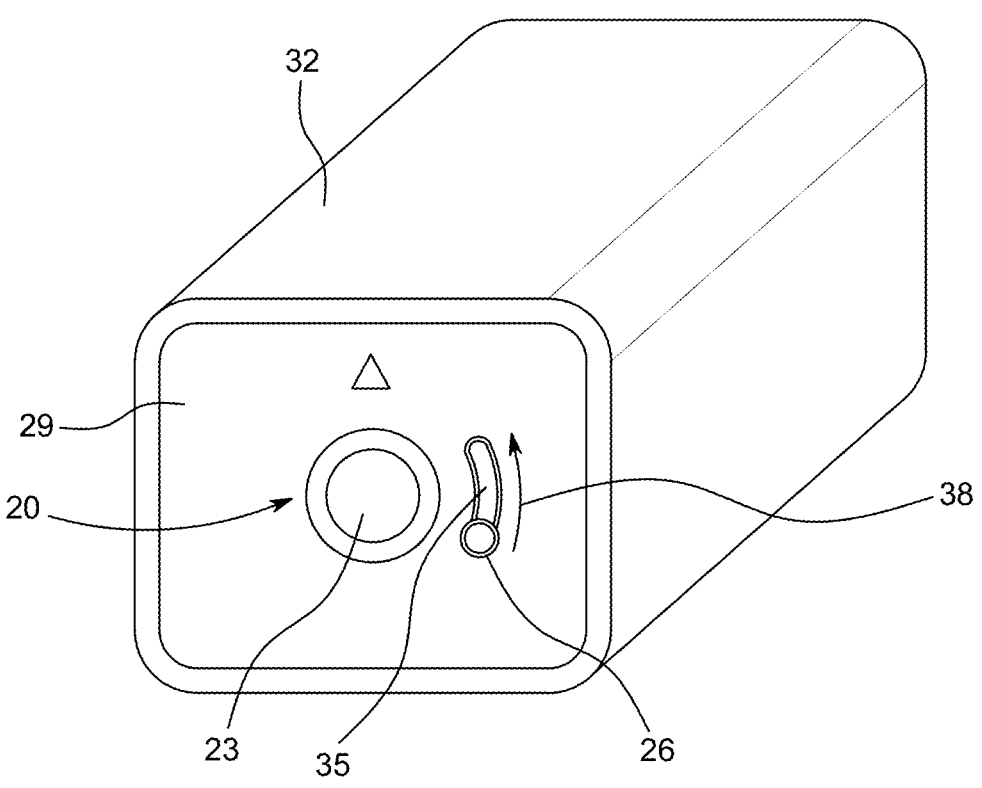
FIG. 1 is a perspective view of a first embodiment of the universal hose attachment mechanism of the present invention shown in the open position.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Embodiments of the present disclosure provide an evacuation unit having housing that maintains a motor. The housing has an opening with an adjustable element (e.g., a mechanical iris, rotatable plate, etc.) that is operable to change the diameter of the opening such that the opening with the adjustable element can be removeably affixed to a tube or hose to create a sealed interface between the opening, the adjustable element and the tube or hose. In practice, the motor is operable to urge or evacuate a fluid (e.g., smoke or air) from a surgical site through the tube or hose and the opening. Thus, the evacuation unit through the adjustable element is able to accommodate tubes or hoses with different diameters. Embodiments of the present disclosure also provide a blower unit and a pump unit that are each operable separately to evacuate or pump a fluid (e.g., smoke or air) from a surgical site. Embodiments further provide that the blower unit and the pump unit can be operably affixed to one another such that they can share the use of each other's filter and/or power and/or user interface.

Figure 2:
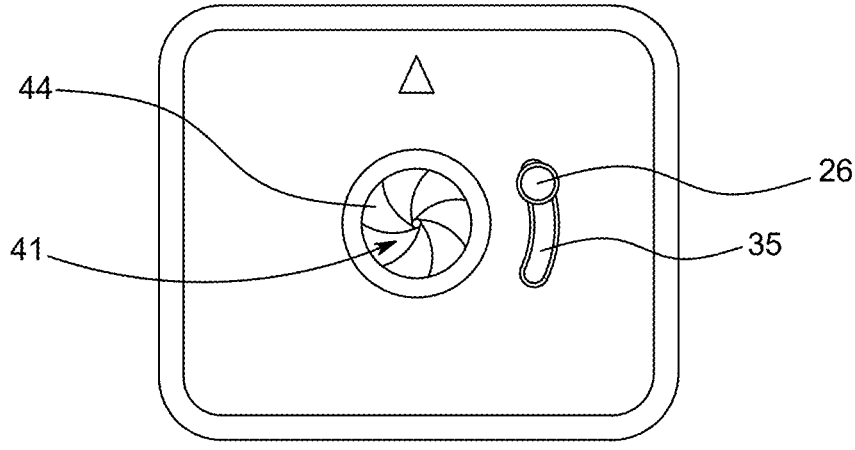
FIG. 2 is a front elevational view of the front of the universal hose attachment of FIG. 1 shown in the closed position.

Referring now to the drawings, and more particularly to FIG. 1 thereof, this invention provides a universal hose attachment mechanism 20 (also referred to as an adjustable element) that adjusts to receive hoses having different diameters (e.g., ⅜"; ¼"; or ⅞"). Depending on the surgical procedure and the instrument being used, the diameter of the suction tube for removing surgical smoke may vary. The attachment mechanism 20 has a central opening 23 for receiving a tube or hose. A knob 26 may be provided on the front panel 29 of the smoke evacuator 32. Pushing the knob 26 along a raceway 35 disposed in the panel 29, in the direction of arrow 38, causes a mechanical iris 41 (FIG. 2) to close around the tube inside the opening 23. Turning to FIG. 2, when the knob 26 is pushed toward the end of the raceway 35, the opening 23 is substantially closed. The mechanical iris 41 is formed from a plurality of curved panels 44 that are constructed from a flexible material capable of sealing the outside surface of the tube. The iris 41 is constructed from the curved panels 44 in a known manner and the position of the iris 41 may be adjusted by means of a gear or the like as will be evident to those of ordinary skill in the art based on this disclosure. The integration of a mechanical iris 41 into the hose inlet for a smoke evacuation system provides numerous advantages including the ability to easily interchange different diameter tubing into the smoke evacuator system.

Figure 3:
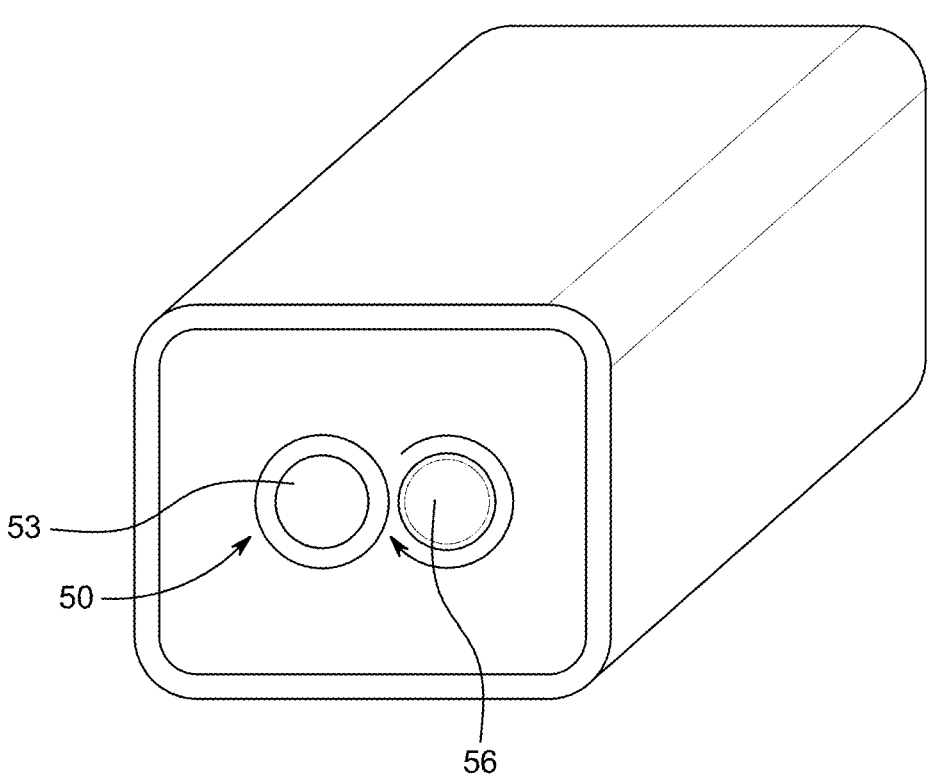
FIG. 3 is a perspective view of an alternate embodiment of the mechanism of FIG. 1 shown in the open position.
Figure 4:
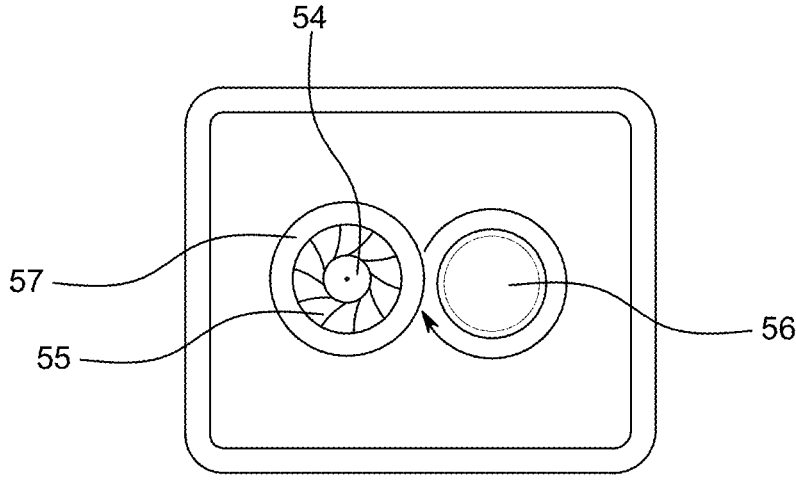
FIG. 4 is a front elevational view of the front of the universal hose attachment of FIG. 3 shown in the closed position.
Figure 5:
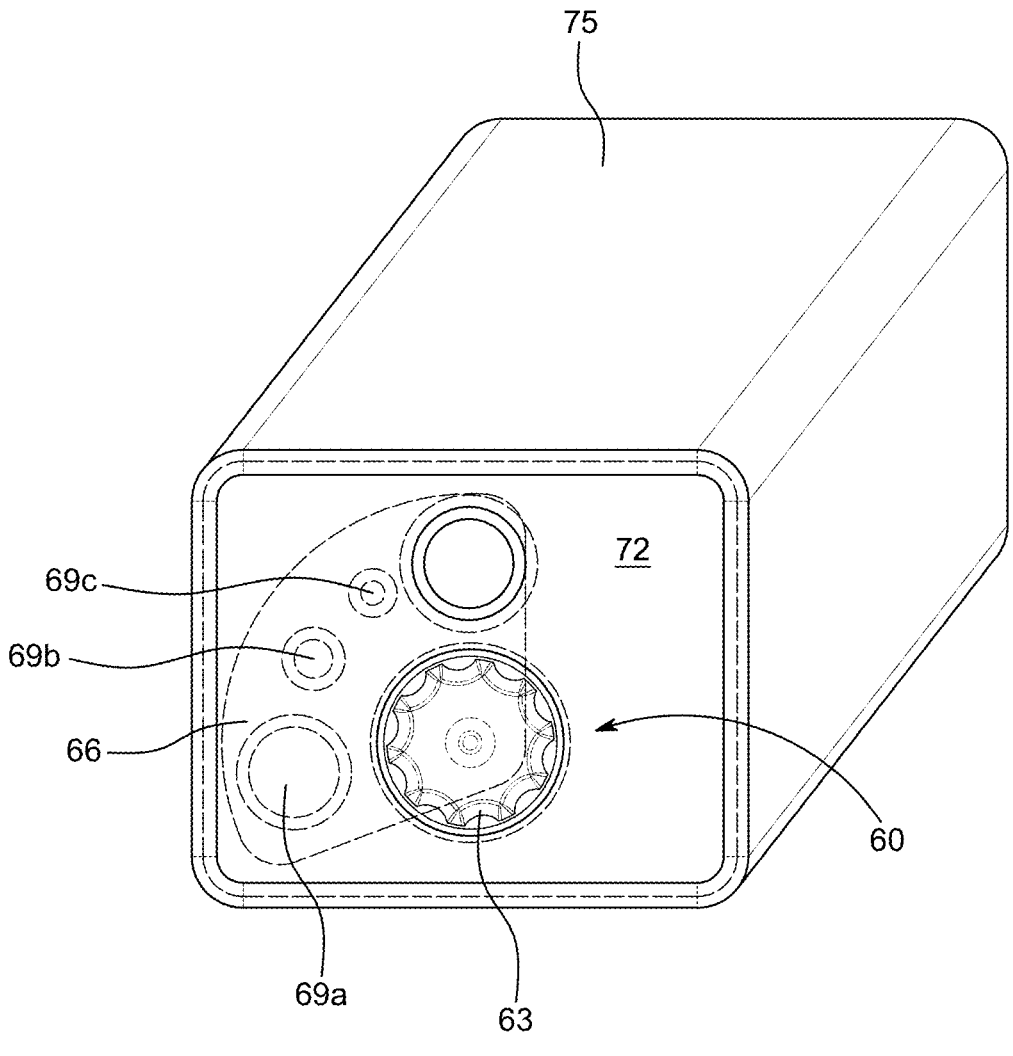
FIG. 5 is a perspective view of another alternate embodiment of the universal hose attachment mechanism of the present invention.

Turning to FIG. 3, an alternate embodiment of the universal hose attachment mechanism provides a mechanism 50 with a central opening 53. The central opening 53 receives a flexible insert 55 (FIG. 4) that is capable of receiving a tube. Once a tube 54 is inserted into the flexible insert 55 in the central opening 53 as shown in FIG. 4, a knob 56 is turned which turns an internal gear. The gear is mechanically connected to a sleeve 57 surrounding the flexible insert 55. When the knob 56 is turned the gear causes the sleeve 57 to be tightened around the flexible insert 55. The tightening of the sleeve 57 causes the flexible insert 55 to compress around the tube 54 to seal it for use.

Figure 6:
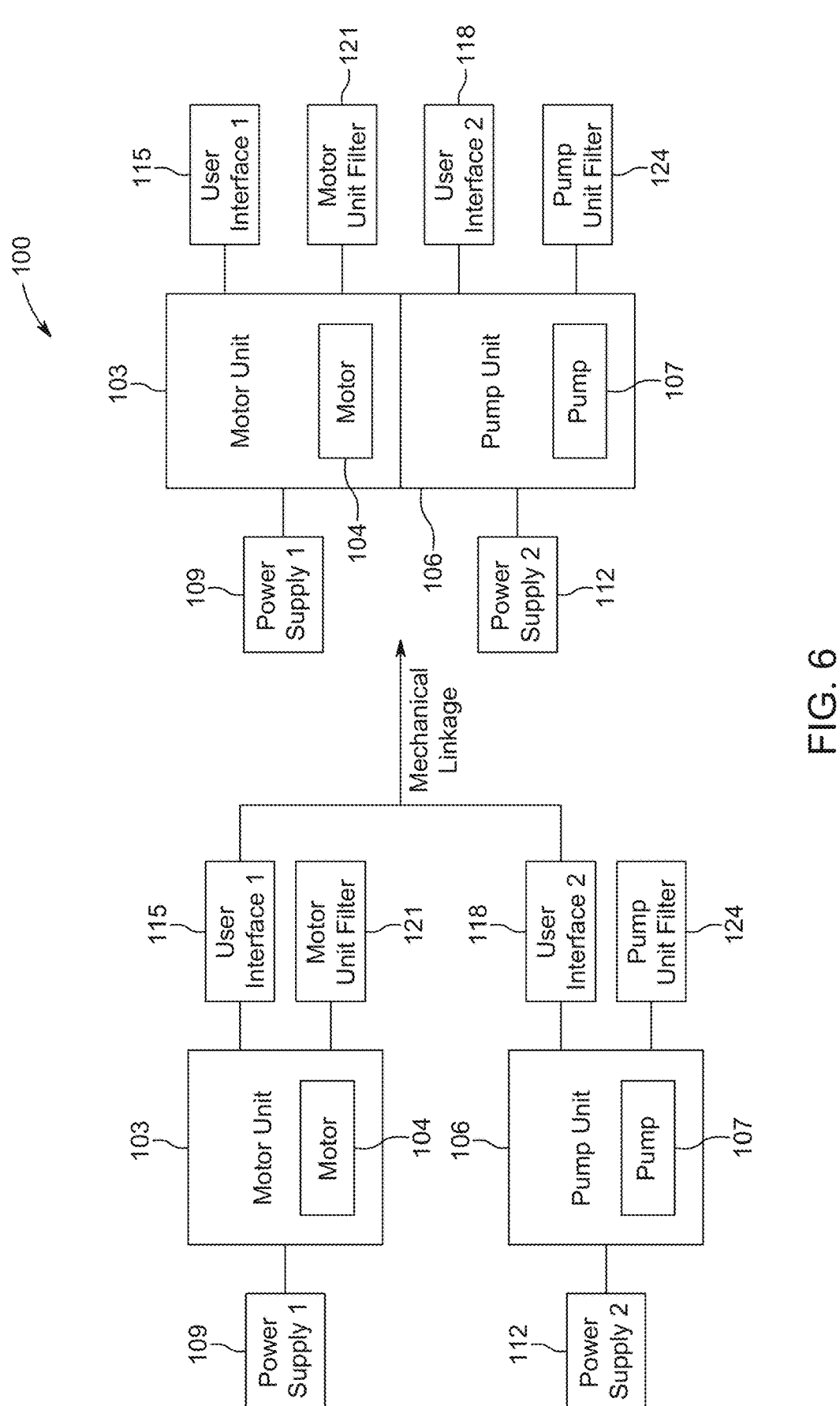
FIG. 6 is a schematic diagram showing a dual surgical smoke evacuator system.

In FIG. 6, a dual surgical smoke evacuator system 100 includes a blower unit 103 with a blower motor 104 and a pump unit 106 with a pump 107. Each unit 103, 106 has separate power sources, interfaces and filters. Blowers and pumps suitable for smoke evacuation systems are known to those of ordinary skill in the art, and specific applications where a blower or pump is suitable are also known. For example, higher volume, lower pressure applications may be suitable for a blower, and a higher pressure, lower volume application may be suitable for a pump. On the left hand side of the figure, the units 103, 106 are shown separate with a first power supply 109 for the blower unit 103 and a second power supply 112 for the pump unit 106. The blower unit 103 has a user interface 115 which allows for setting parameters associated with the blower unit 103 such as the speed of the motor. The pump unit 106 has a user interface 118 that provides for control of the pump unit 106 by the user. The blower unit 103 has a filter assembly 121, and the pump unit 106 has a filter assembly 124. As shown in the right hand side of the figure, the two units 103, 106 may be physically combined into a single attached system. When the units 103, 106 are attached, they form a dual smoke evacuation system that is capable of providing for smoke evacuation from either a blower unit 103 or a pump unit 106 depending on the application and the system requirements.

Figure 7:
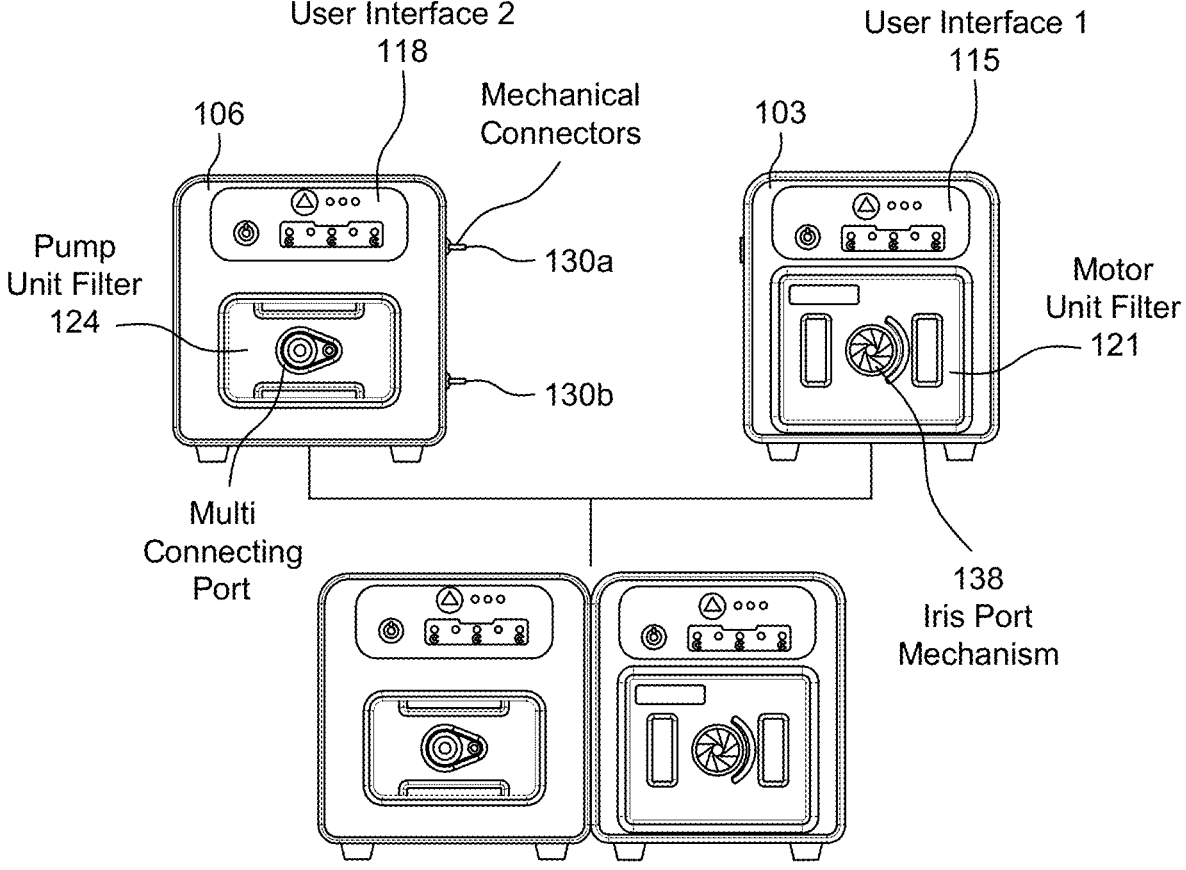
FIG. 7 is a front elevational view of the dual surgical smoke evacuator system of FIG. 6.
Figure 8:
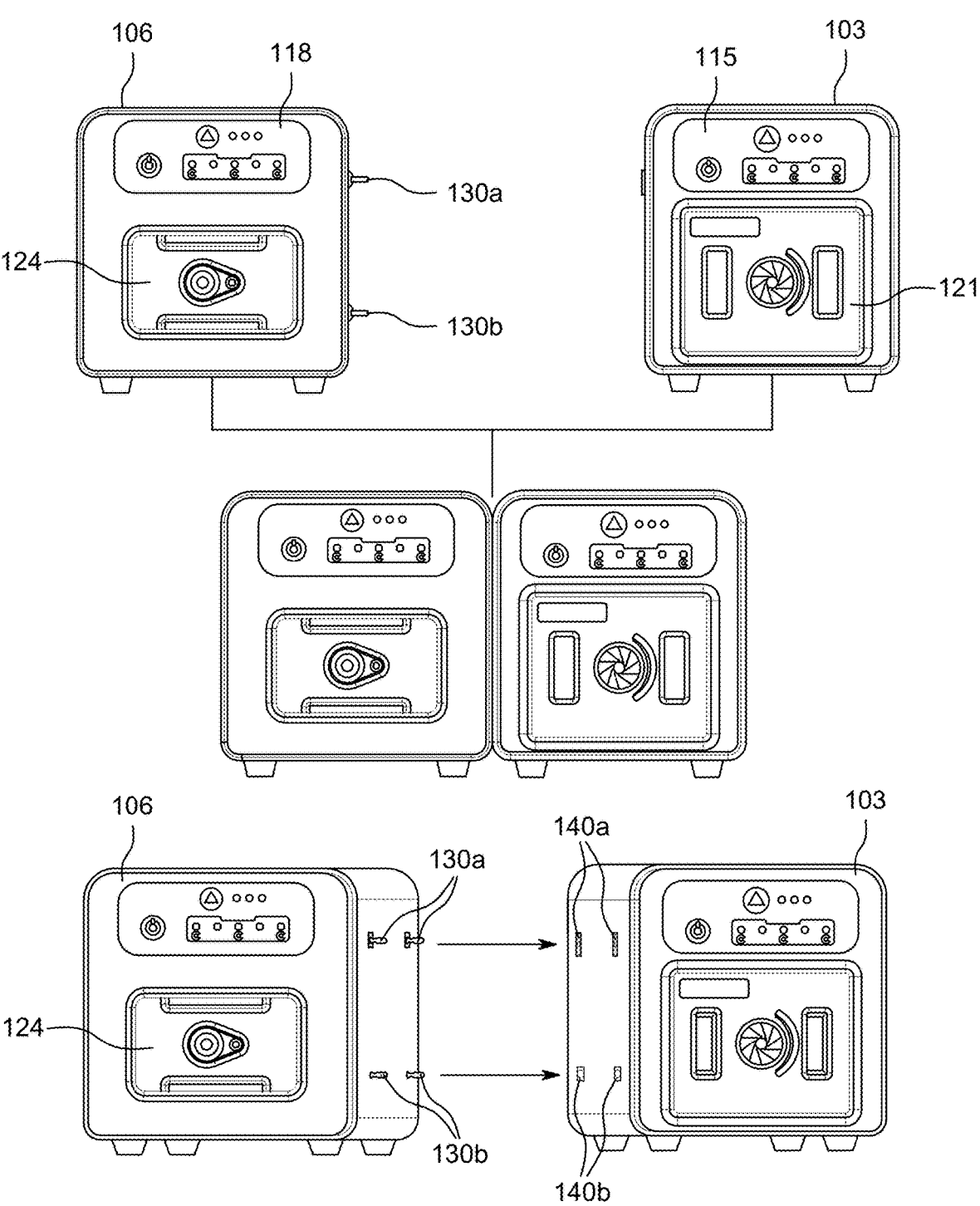
FIG. 8 is another front elevational view of the dual surgical smoke evacuator system of FIG. 6.
Figure 9:
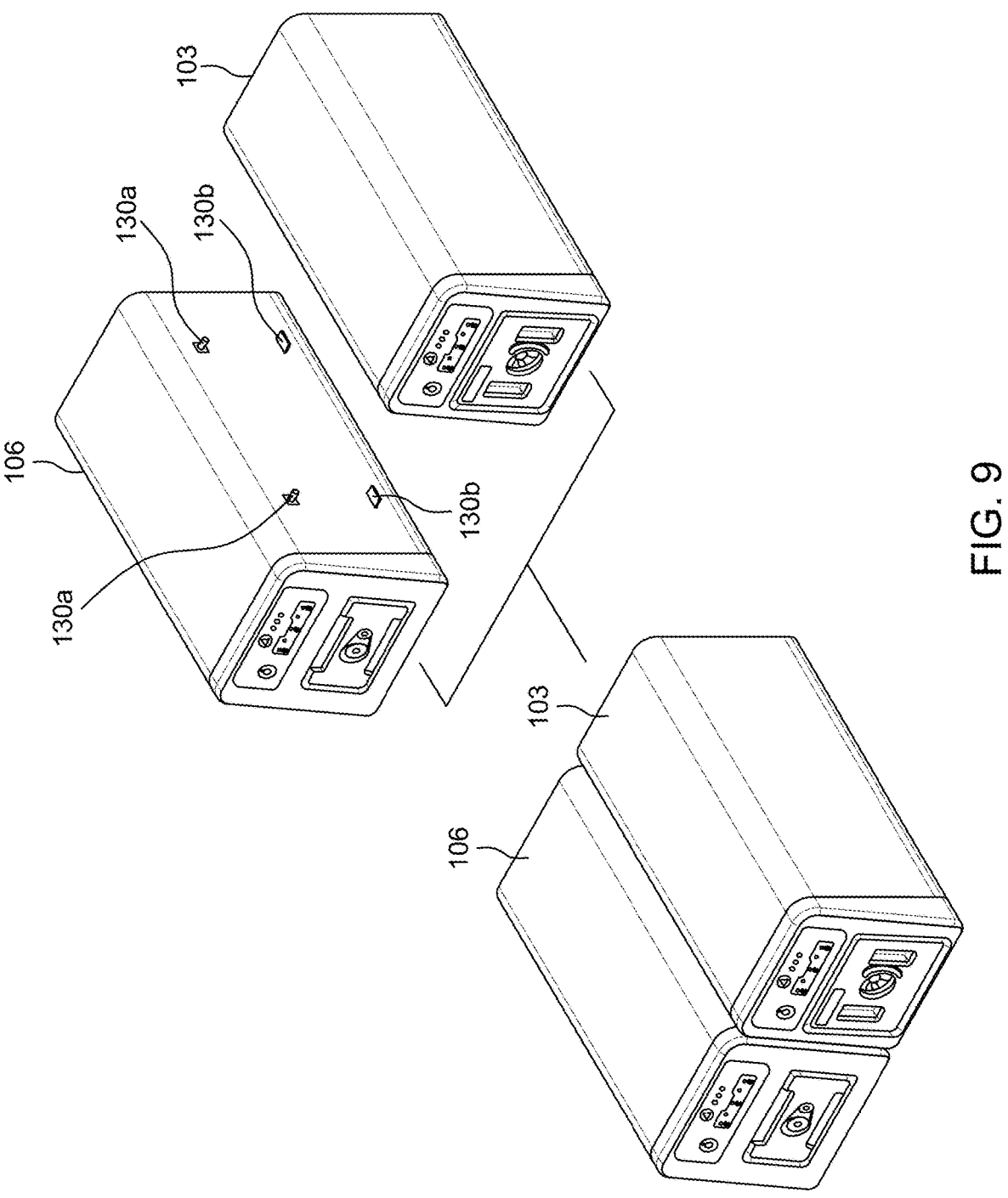
FIG. 9 is a perspective view of the dual surgical smoke evacuator system of FIG. 6.
Figure 10:
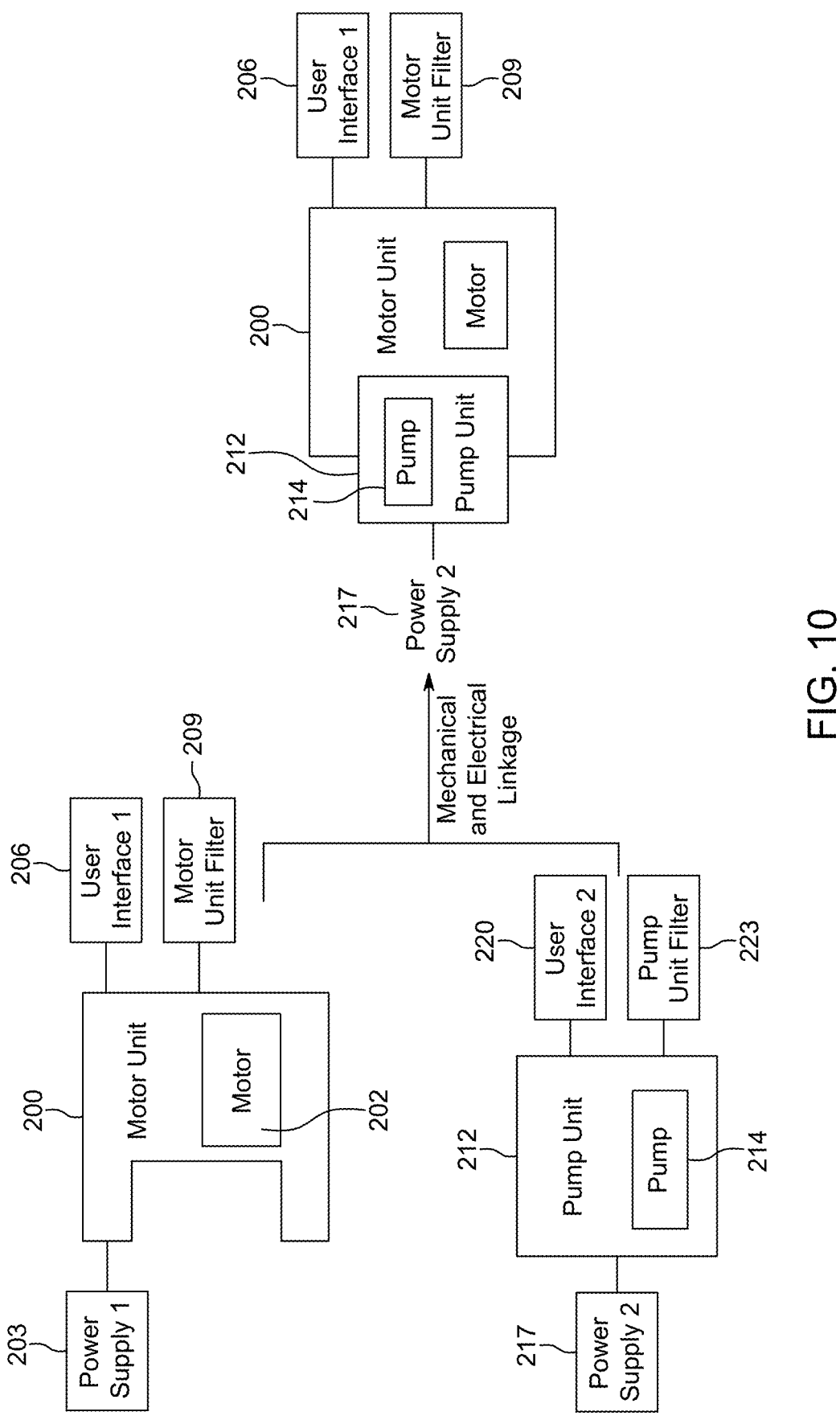
FIG. 10 is a schematic of an alternative embodiment of the dual surgical smoke evacuator system.

Turning to FIGS. 7-9, the blower unit 103 and pump unit 106 may be provided with mechanical connectors 130a and 130b such as male/female connectors on the housing to provide for detachably connecting the units. When the units 103, 106 are connected in side-by-side fashion as shown in FIG. 7, the user may select either unit for the specific application. The units 103, 106 may be provided with a universal hose attachment mechanism 138 as described above for receiving tubes having different diameters for different smoke removal applications and flow rates. As shown in FIG. 8, connectors 130a, 130b may engage with openings 140a and 140b to connect the blower unit 103 to the pump unit 106.

In FIGS. 10-14, an alternate embodiment of the dual smoke evacuation system is shown. This embodiment provides two separate blower and pump units that can operate separately or that can be connected both mechanically and electrically to form a single combined unit. The units have separate power sources, separate interfaces and separate filters when apart, but share a power source, filter, and user interface when linked together. A blower unit 200 includes a blower motor 202, a power supply 203, a user interface 206, and a filter assembly 209. A pump unit 212 includes a pump 214, a power supply 217, a user interface 220, and a filter assembly 223. The two units 200 and 212 may be used separately and individually or may be combined into a single unit capable of being used in either a pump or blower mode. As illustrated, the two units 200 and 212 may be combined by removing the filter assembly 223 from the pump unit 212 and mounting the pump unit 212 onto the blower unit 200. The combined unit utilizes user interface 206 and filter assembly 209.

Figure 11:
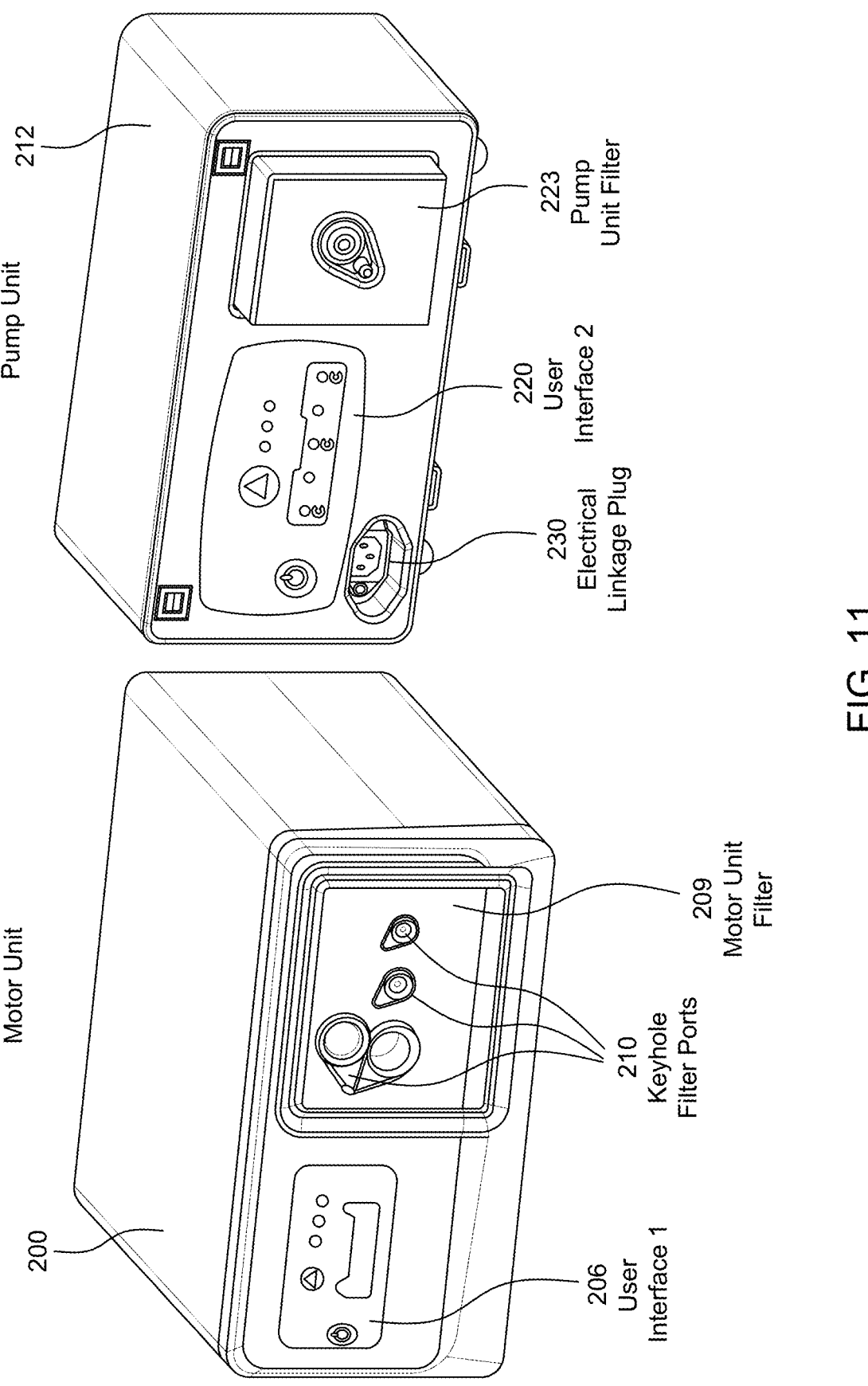
FIG. 11 is a perspective view of the dual surgical smoke evacuator system of FIG. 10.

Turning to FIG. 11, on the left hand side of the figure, the blower unit 200 includes the filter assembly 209 which has keyhole inlet ports 210 for receiving a tube for evacuation of surgical smoke. The tube conveys surgical smoke from the surgical theater to the unit 200 by means of suction created by the dual smoke evacuation system or the blower unit 200. On the right hand side of FIG. 11, the pump unit 212 is shown with an electrical linkage plug 230 disposed on the front panel. Filter assembly 223 is located on the right hand side of unit 212 and may be removed. Filter assembly 223 also includes an air inlet 225 for connection to a tube for conveying surgical smoke.

Figure 12:
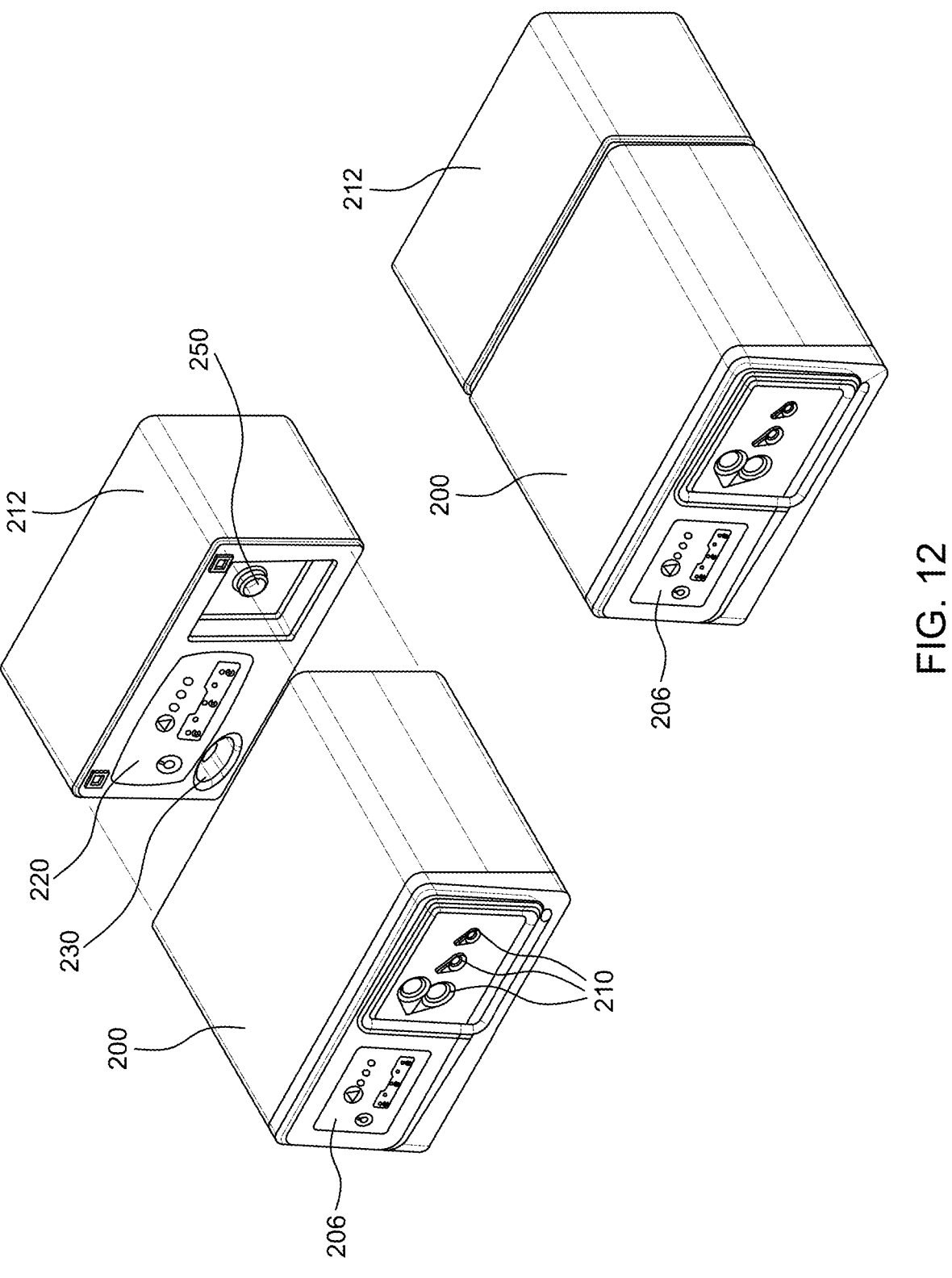
FIG. 12 is another perspective view of the dual surgical smoke evacuator system of FIG. 10.
Figures 13, 14:
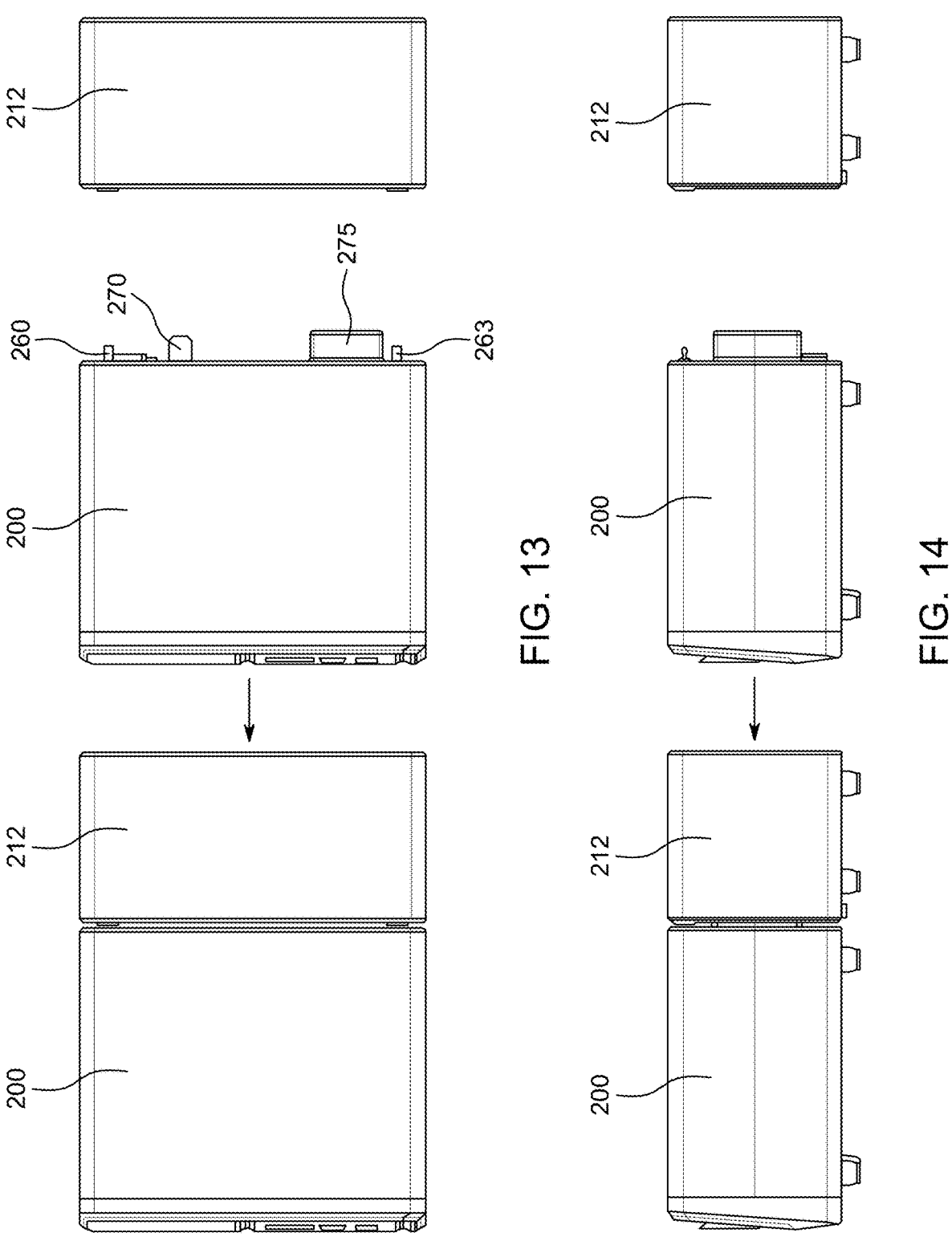
FIG. 13 is a top plan view of the dual surgical smoke evacuator system of FIG. 10.
FIG. 14 is a side elevational view of the dual surgical smoke evacuator system of FIG. 10.

Turning to FIG. 12, with the filter assembly 223 removed, the pump unit 212 may be attached to the rear of the blower unit 200. An electrical connector 270 (FIG. 13) for the blower unit 200 is connected to the electrical linkage plug 230 so that power to both units may be supplied by power supply 217. An air inlet 250 is disposed at the front of the pump unit 212 where the filter assembly 223 has been removed. The air inlet 250 engages with an outlet 275 in the blower unit 200. User interface 206 includes a control for selecting either the blower unit 200 or the pump unit 212 to convey the surgical smoke. FIGS. 13-14 show the conversion of the individual units into a single dual smoke evacuation system. The blower unit 200 may be provided with mechanical connectors 260, 263 for engaging with corresponding openings in the pump unit 212. The electrical connector 270 engages with the electrical linkage plug 230. The air outlet 275 engages with the air inlet 250 on the pump unit 212.

This disclosure has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. An apparatus for evacuation, the apparatus comprising:
   (a) a blower having a housing that maintains a motor, a user interface, an opening, a blower power supply, a filter, a blower connector, and an adjustable element, the motor operable to urge a fluid to pass through the opening and the adjustable element, the filter operable to filter extraneous materials from the fluid that passes through the opening and the adjustable element, the adjustable element operable to change a size of the opening to a plurality of different diameters, the user interface operable to control the motor; and
   (b) a pump having a housing that maintains a pump motor, a pump user interface, a pump port, a pump power supply, a pump connector, and a pump filter, the pump motor operable to urge a fluid to pass through the pump port, the pump filter operable to filter extraneous materials from the fluid that passes through the pump port, wherein the blower connector and the pump connector are operable to be removably coupled to each other thereby affixing the blower and the pump, wherein the user interface is operable to control the motor and the pump motor when the blower connector and the pump connector are coupled to each other, and wherein the pump user interface is obstructed by the blower when the blower connector and the pump connector are coupled to each other, and wherein the pump user interface is operable to control the pump when the blower connector and the pump connector are not coupled to each other.

2. The apparatus according to claim 1, wherein the blower connector and the pump connector mechanically and electrically connect the blower and the pump.

3. The apparatus according to claim 1, wherein the blower power supply is operable to provide power to the blower and the pump when the blower connector and the pump connector are coupled to each other.

4. The apparatus according to claim 1, wherein the filter is operable to filter extraneous materials from a fluid that passes through the opening and a fluid that passes through the pump port when the blower connector and the pump connector are coupled to each other.

5. The apparatus according to claim 1, wherein the blower and the pump are operable to evacuate a fluid from a surgical site.

6. The apparatus according to claim 1, wherein the adjustable element comprises a plate having a plurality of different sized holes rotatably affixed to the housing, and wherein the plate is operable to locate each one of the plurality of different sized holes with the opening.

7. An apparatus for evacuation, the apparatus comprising:
   (a) a blower having a housing that maintains a motor, a user interface, an opening, a blower power supply, a filter, a blower connector, and an adjustable element, the motor operable to urge a fluid to pass through the opening and the adjustable element, the filter operable to filter extraneous materials from the fluid that passes through the opening and the adjustable element, the adjustable element operable to change a size of the opening to a plurality of different diameters, the user interface operable to control the motor; and (b) a pump having a housing that maintains a pump motor, a pump user interface, a pump port, a pump power supply, a pump connector, and a pump filter, the pump motor operable to urge a fluid to pass through the pump port, the pump filter operable to filter extraneous materials from the fluid that passes through the pump port, wherein the blower connector and the pump connector are operable to be removably coupled to each other thereby affixing the blower and the pump, and wherein the pump user interface is obstructed by the blower when the blower connector and the pump connector are coupled to each other, and wherein the user interface and the pump user interface are both operable when the blower connector and the pump connector are coupled to each other, and wherein the pump user interface is operable to control the pump when the blower connector and the pump connector are not coupled to each other.

8. The apparatus according to claim 7, wherein the blower connector and the pump connector mechanically and electrically connect the blower and the pump.

9. The apparatus according to claim 7, wherein the blower power supply is operable to provide power to the blower and the pump when the blower connector and the pump connector are coupled to each other.

10. The apparatus according to claim 7, wherein the blower and the pump are operable to evacuate a fluid from a surgical site.

11. The apparatus according to claim 7, wherein the adjustable element comprises a plate having a plurality of different sized holes rotatably affixed to the housing, and wherein the plate is operable to locate each one of the plurality of different sized holes with the opening.

* * * * *